United States Patent

Maaskamp

[11] Patent Number: 5,993,409
[45] Date of Patent: Nov. 30, 1999

[54] NEEDLE FOR SURGICAL USE

[75] Inventor: Armand Maaskamp, Mission Viejo, Calif.

[73] Assignee: Surgin Surgical Instrumentation, Inc., Tustin, Calif.

[21] Appl. No.: 08/977,726

[22] Filed: Nov. 25, 1997

Related U.S. Application Data

[60] Provisional application No. 60/031,939, Nov. 27, 1996.

[51] Int. Cl.$^6$ .................................................. A61B 17/20
[52] U.S. Cl. ................................................ 604/22; 604/27
[58] Field of Search .................................. 604/22, 27, 35, 604/43, 44, 48, 272, 294, 313, 164, 239, 264, 274

[56] References Cited

U.S. PATENT DOCUMENTS

| | | |
|---|---|---|
| 3,526,219 | 9/1970 | Balamuth . |
| 3,589,363 | 6/1971 | Banko et al. . |
| 4,136,700 | 1/1979 | Broadwin et al. . |
| 4,301,802 | 11/1981 | Poler . |
| 4,465,470 | 8/1984 | Kelman . |
| 4,518,383 | 5/1985 | Evans . |
| 4,674,500 | 6/1987 | DeSatnick . |
| 4,689,040 | 8/1987 | Thompson . |
| 4,750,488 | 6/1988 | Wuchinich et al. . |
| 4,832,683 | 5/1989 | Idemoto et al. . |
| 5,084,012 | 1/1992 | Kelman . |
| 5,154,694 | 10/1992 | Kelman . |
| 5,284,476 | 2/1994 | Koch . |
| 5,417,654 | 5/1995 | Kelman . |
| 5,458,614 | 10/1995 | Humphrey . |
| 5,514,113 | 5/1996 | Anderson et al. . |
| 5,653,724 | 8/1997 | Imonti . |

OTHER PUBLICATIONS

Supplement to the Feb. 1, 1994 issue of Ocular Surgery News, article entitled "Inventor of phaco hails current state of the art, sees ongoing role for technique".
Copy of International Search Report issued in connection with Applicant's corresponding PCT application S/N PCT/US97/22332 filed on Nov. 25, 1997.

*Primary Examiner*—Wynn Wood Coggins
*Assistant Examiner*—Kevin C. Sirmons
*Attorney, Agent, or Firm*—Raymond A. Bogucki

[57] ABSTRACT

A surgical needle for use in phaco-emulsification procedures during eye surgery is disclosed. The surgical needle comprises a tubular principal section substantially concentric about a longitudinal principal axis and a tubular terminal section for channeling aspiration flow away from the surgical site. The terminal section is angled with respect to the principal section to access a greater area of the surgical site. The angled terminal section also presents an angled side face to the reciprocating motion when the surgical needle is reciprocated along the principal axis, causing increased cavitational emulsification. An aspiration bore at an extreme distal end of the terminal receives the aspiration flow. The aspiration bore has two planar end faces, one to minimize the possibility of accidental tearing of eye tissue, and the other to open up the aspiration bore to the direction of reciprocation and maximize the occlusion and mechanical cavitation of material.

9 Claims, 2 Drawing Sheets

NEEDLE FOR SURGICAL USE

CROSS-REFERENCE TO RELATED APPLICATIONS

This invention relates to Provisional Application Ser. No. 60/031,939, filed Nov. 27, 1996. The contents of that application are incorporated by reference herein.

BACKGROUND OF THE INVENTION

1. Field of the Invention

This invention relate to surgical needles, and more particularly to needles used in phaco-emulsification procedures during eye surgery.

2. Description of Related Art

In a number of surgical procedures, the tip of a small needle is inserted into body tissue or a cavity and used to remove unwanted material, often with the assistance of ultrasonic mechanical vibration. One prominent example of this type of application is the phaco-emulsification procedure, adopted several decades ago, for the removal of cataracts and other material from the capsular bag of the eye, particularly to facilitate an artificial lens implant. In the earliest examples of this procedure, a straight needle was inserted through a small incision into the capsular bag, and ultrasonic oscillation of the needle tip caused the tip to contact and mechanically emulsify the material. In addition, the ultrasonic oscillation of the needle tip in the liquid of the capsular bag caused a small amount of cavitational emulsification of the material.

An aspiration bore in the center of the needle drew out the material as it was emulsified. The suction effect of the aspiration flow in the aspiration bore created a pressure differential between the inside and outside of the needle and caused material to occlude at, and adhere to, the needle tip, an effect that was generally beneficial because the adhesion helped the tip contact and mechanically emulsify the adhering material. In addition, the peristaltic pump that generated the aspiration flow would increase the suction upon detection of an occlusion, thereby facilitating removal of the occlusion. The aspiration of emulsified material concurrent with the emulsification process enabled the complete procedure to be effected within a relatively short interval. Due to the small incisions and limited invasiveness, there were minimal side effects and very short recovery time under ideal conditions.

Ideal conditions, however, were rarely available, and as many thousands of these operations were completed, it was found desirable to use one or more of a number of variations for different purposes, not all of which are compatible. For example, the interior volume of the capsular bag is of maximum depth in the mid-region, into which a straight needle can conveniently be inserted. Alongside the incision in the anterior capsular bag wall and in the corners of the capsular bag, however, access can better be obtained by a curved or bent needle. Accordingly, a number of different variants on the curved needle were introduced, as evidenced in part by U.S. Pat. Nos. 4,750,488; 4,301,802; 4,136,700; 5,154,694 and 5,417,654, in which different variations were used for different purposes and advantages. In addition, it was found that curved or bent needles could improve cavitational emulsification, because cavitation increases when the larger surface area presented by the side of the curved or bent needle moves in opposition to the material. Some of the curvatures were also intended to reduce the danger that the cutting edge of the tip would encounter and damage the rear wall of the capsular bag as the needle was manipulated within the capsular bag.

Such changes, however, introduce other problems and limitations in practical situations. Conventional needles have a sloping face terminating in a sharp point to aid in puncturing tissue. Simply bending such a needle to a desired angle may result in the sharp point facing the capsular bag wall in certain needle orientations, thereby increasing the chance of damage to the capsular bag wall.

A curved or bent needle also decreases the surgeon's visibility of the needle tip. Typically, a surgeon operates from above the eye, pointing the needle downward into the eye with the bend in the needle pointing downward. When viewed from above, the tip of a needle with a severe bend tends to disappear underneath the body of the needle, decreasing its visibility and increasing the danger of positioning error by the surgeon.

In addition, the aspiration bore of bent or curved needles often faces away from the direction of reciprocation, and thus does not present a large opening in the direction of reciprocation upon which the material may be occluded. Furthermore, the sharp point created by the sloping face of bent conventional needles may not allow the aspiration bore to be placed in close proximity to material in certain orientations, thereby decreasing occlusion of material at the aspiration bore. The bend of the needle also increases frictional contact of the aspiration flow with the interior walls of the needle, which increases flow resistance, decreases the aspiration rate, and reduces the occlusion of material at the aspiration bore. The reduced occlusion and adhesion of material to the needle tip resulting from bent or curved needles ultimately decreases the efficiency of emulsification, increases the required operating time, and increases the possibility of heat damage or other damage to the eye. To offset the reduced occlusion of bent needles, aspiration pressure may be increased. However, increased aspiration pressure makes the phaco-emulsification procedure less controllable and increases the danger of collapsing the capsular bag.

The effect of curved or bent needles on capsular bag access, cavitational emulsification, puncture avoidance, tip visibility, aspiration rate, occlusion, and mechanical emulsification therefore varies as the curvature or bend in the needle increases. As the curvature or bend increases, capsular bag access and cavitational emulsification increase, while tip visibility, aspiration rate, occlusion, and mechanical emulsification generally decrease. Consequently, there is a need for a needle offering the advantages of better cavitational emulsification, easier manipulation and access within the capsular bag, and lessened chance of unintended puncturing of the back wall of the capsular bag, while at the same time providing an aspiration bore orientation and flow rate that facilitates occlusions at the needle tip and enhanced mechanical emulsification.

SUMMARY OF THE DISCLOSURE

In accordance with the invention, an improved needle is provided by a structure having a tubular, substantially straight principal section and, near the distal end, a tubular, substantially straight terminal section approximately 5 mm in length, bent at approximately a 5°–35° angle with respect to the principal section and having two differently angled end faces about an aspiration bore at its extreme distal end. The two end faces slant oppositely away from a plane lying perpendicular to the longitudinal axis of the terminal section, one face being at approximately a 0–20° angle to the plane, and the other at approximately a 10–45° angle to the plane.

The 5°–35° angle of the bend in the needle and the 5 mm length of the bent portion of the needle allows a surgeon to rotate the needle and increase access to the capsular bag, while creating increased cavitational emulsification due to the larger surface area presented by the side of the bent needle to the targeted material. However, the angle is not so severe as to substantially impair visibility of the tip when viewed from above, nor substantially impair the aspiration flow rate within the needle.

The 10–20° angle of one end face of the needle presents a substantially parallel face to the capsular bag wall in certain needle orientations, decreasing the chance of puncturing the capsular bag wall. In addition, the angle allows the aspiration bore to be placed in close proximity with the material to be emulsified, thereby increasing occlusion of the aspiration bore with the material and enhancing mechanical emulsification.

The 10°–45° angle of the other end face of the needle opens up the aspiration bore to the direction of needle reciprocation, allowing the aspiration bore to be placed in close proximity with the material to be emulsified, increasing occlusion of the aspiration bore with the material and enhancing mechanical emulsification.

BRIEF DESCRIPTION OF THE DRAWINGS

A better understanding of the invention may be had by reference to the following description, taken in conjunction with the accompanying drawings, in which.

DETAILED DESCRIPTION OF THE INVENTION

Figure 1:
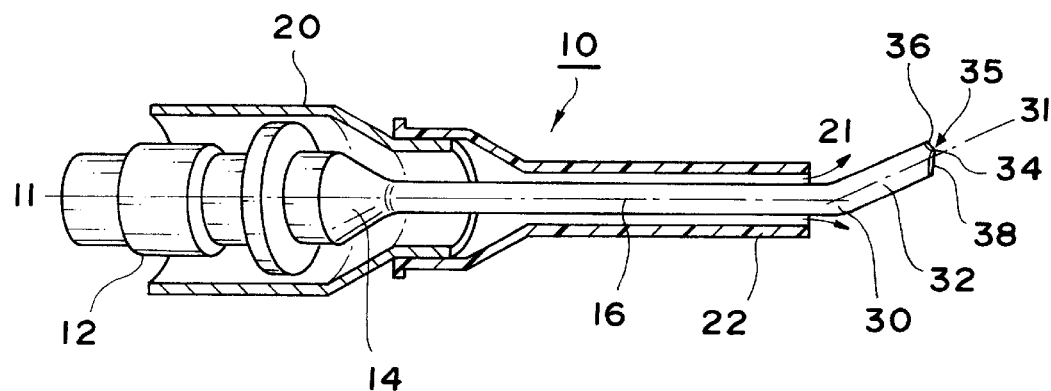
FIG. 1 is a perspective view, partially broken away, of an example of an improved needle for ophthalmic surgery in accordance with the invention.

Referring now to FIG. 1, a needle 10 extending from a conventional handpiece (not shown) is substantially concentric about a longitudinal principal axis 11 and includes an end fitting 12 for attachment to the handpiece and a transition section 14 that tapers down to a small diameter and substantially straight principal section 16, typically of less than 3 mm diameter because incisions are of 3 mm or less in length. The body of the handpiece includes a housing 20 (shown only partially) about the needle 10, providing an outer concentric pathway for an irrigation fluid flow 21. The irrigation fluid is confined about the exterior of the principal section 16 by a sleeve 22 of elastomeric or other flexible material. The hollow interior of the principal section 16 receives an aspiration flow 35 countercurrent to the irrigation fluid flow 21.

It should be understood that the configuration of the end fitting 12, transition section 14, housing 20, and sleeve 22 of FIG. 1 are merely exemplary. They may be configured in any design which is compatible with known ultrasonic surgical tool devices.

Figure 2:
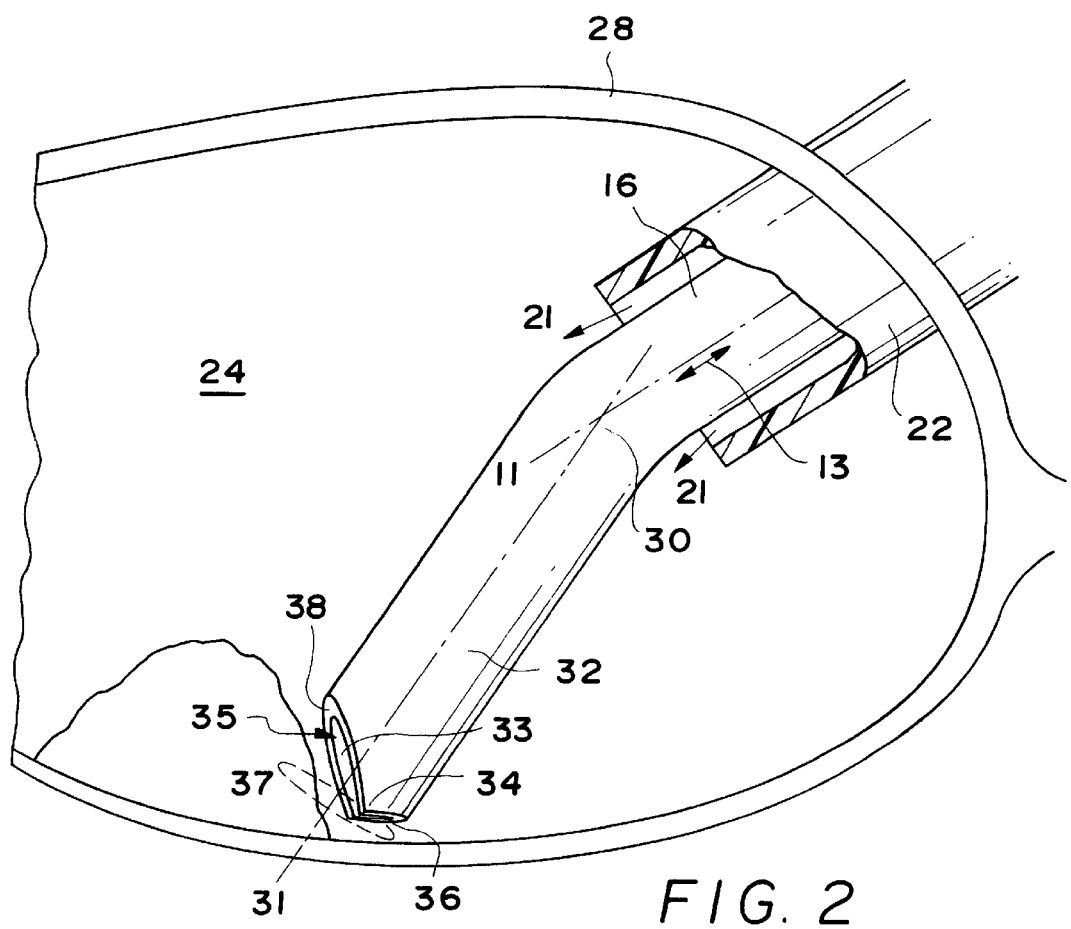
FIG. 2 is an enlarged view of the surgical needle tip inserted in a capsular bag, useful in explaining the operation of the invention.

Referring now to FIG. 2, the principal section 16 of the needle merges near its distal end into a curved section 30, and then into a substantially straight terminal section 32 approximately 5 mm long that is substantially concentric about a longitudinal terminal axis 31, whereby the terminal axis 31 forms an angle to the principal axis II of approximately 5° to 35°. The extreme distal end of the terminal section 32 has an apex 34, and end faces about an aspiration bore 33 which are planar but differently slanted relative to the apex 34. The first end face 36 is slanted so as to be at an angle approximately 0°–20° (here about 10°) relative to a plane 37 lying perpendicular to the terminal axis 31, whereas the second end face 38 is slanted to be at an angle approximately 10°–45° (here about 45°), in an opposite sense, relative to that axis. Aspiration flow 35 enters the aspiration bore 33 and flows through the terminal section 32 and curved section 30 to the principal section 16.

Figure 3:
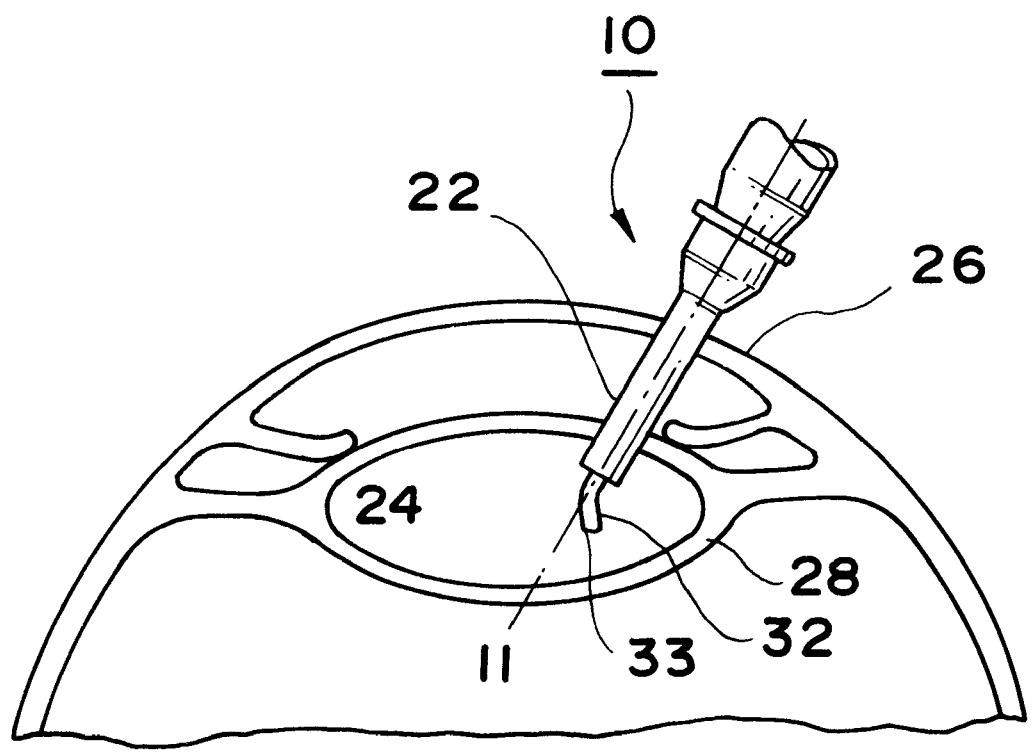
FIG. 3 is a somewhat idealized sectional view of the surgical needle of FIG. 1 as inserted into a capsular bag during surgery.

As illustrated in FIG. 3, this arrangement enables the surgical needle 10 to be utilized within a capsular bag 24 through small incisions in a cornea wall 26 and a capsular bag wall 28. Inserted through these incisions, the elastomeric or other flexible material of the sleeve 22 contacts the walls of the incision made in the cornea wall 26 and capsular bag wall 28 and allows the needle 10 to be moved to a limited extent along or transversely to the principal axis 11 and angled to different positions. The terminal section 32 also enables the aspiration bore 33 to be rotated 360° about the principal axis 11 to reach a large circular area within the capsular bag 24. This flexibility of movement, along with the 5 mm length of the terminal section 32, ensures adequate access to the interior of the capsular bag 24.

Referring again to FIG. 2, the terminal section 32 presents an angled side face 29 to the direction of reciprocation 13, creating increased cavitation bubbles in the liquid of the capsular bag 24 and consequent increased cavitational emulsification upon their collapse. However, the terminal section 32 is not bent so severely as to become hidden underneath the principal section 16 and substantially impair a surgeon's visibility of the aspiration bore 33 when viewed from above, nor does it substantially impair the aspiration flow 35 within the needle 10.

The 10°–45° angle of the second end face 38 opens up the aspiration bore 33 to the direction of reciprocation 13 and allows the aspiration bore 33 to be placed in close proximity with the material to be emulsified. The suction effect of the aspiration flow 35 in the aspiration bore 33 creates a pressure differential between the inside and outside of the terminal section 32 and causes material to occlude at, and adhere to, the aspiration bore 33. This occlusion is beneficial because the adhesion helps the first and second end faces 36, 38 maintain contact with, and mechanically emulsify, the adhering material. The increased occludability of the aspiration bore 33 engendered by the angle of the second end face 38 allows sufficient occlusion to occur without having to increase aspiration flow rates, a situation preferred by surgeons because the phacoemulsification process is more controllable at low aspiration flow rates.

If the extreme distal end of the terminal section 32 is placed closely adjacent to the capsular bag wall 28 as shown in FIG. 2, the risk of puncture is diminished because the 0°–20° angle of the first end face 36 presents a substantially parallel face to the capsular bag wall 28. In addition, the angle of the first end face 36 may allow the aspiration bore 33 to be placed in closer proximity with material to be emulsified, thereby increasing the occlusion of the aspiration bore 33 with the material and increasing mechanical emulsification.

Because of the aforementioned features of the invention, emulsification of material in the capsular bag 24 can be effected more efficiently, with greater safety, in a shorter time span and with lower investment of energy, and therefore with decreased heat and decreased possibility of damage to the material.

The above description of the present invention are for illustrative purposes. Variations will be apparent to those skilled in the art. In addition, the invention can be practiced in the absence of any element not specifically disclosed. The invention includes all forms and variations within the scope of the appended claims.

What is claimed is:

1. A surgical needle for use in phaco-emulsification procedures during eye surgery, the surgical needle comprising:
    a tubular principal section, substantially concentric about a longitudinal principal axis, for receiving an aspiration flow, wherein the surgical needle is ultrasonically reciprocated along the principal axis for mechanically and cavitationally emulsifying and aspirating eye tissue within a capsular bag;
    a tubular curved section merged with the principal section for channeling the aspiration flow to the principal section;
    a tubular terminal section having an angled side face, substantially concentric about a longitudinal terminal axis and merged with the curved section for channeling the aspiration flow to the curved section, wherein the terminal axis is angled with respect to the principal axis; and
    an aspiration bore at an extreme distal end of the terminal section for receiving the aspiration flow, the aspiration bore having a planar first end face and a planar second end face, the planar end faces having different orientations relative to a plane transverse to the longitudinal terminal axis.

2. The surgical needle of claim 1, wherein the terminal axis forms an angle of approximately 5° to 35° with respect to the principal axis for accessing an extended volume within the capsular bag when the surgical needle is rotated about the principal axis, for presenting the angled side face of the terminal section to eye tissue and increasing cavitational emulsification when the surgical needle is reciprocated along the principal axis, for maintaining visibility of the aspiration bore when viewed from above, and for maintaining a sufficient aspiration flow rate.

3. The surgical needle of claim 1, wherein the planar second end face is tapered back at an angle of approximately 10°–45° with respect to a plane lying perpendicular to the terminal axis for opening up the aspiration bore to the direction of reciprocation, allowing the aspiration bore to be placed in close proximity with material to be emulsified, causing material to occlude and adhere to the aspiration bore, and helping the second end face to maintain contact with and mechanically emulsify the adhering material.

4. The surgical needle of claim 1, wherein the planar first end face is tapered back at an angle of approximately 0°–20° with respect to a plane lying perpendicular to the terminal axis for allowing the aspiration bore to be placed in close proximity with material to be emulsified, thereby increasing occlusion at the aspiration bore and increasing mechanical emulsification, and for presenting the first end face at a nearly parallel orientation to a capsular bag wall when the surgical needle is positioned close to the capsular bag wall to minimize the possibility of tearing the capsular bag wall.

5. The surgical needle of claim 1, wherein the terminal section is approximately 5 mm long for accessing an adequate interior volume of the capsular bag when the surgical needle is rotated about the principal axis.

6. A needle for use with a surgical apparatus, the needle comprising:
    a tubular principal section, substantially concentric about a longitudinal principal axis for receiving an aspiration flow, wherein the needle is ultrasonically reciprocated along the principal axis for mechanically and cavitationally emulsifying and aspirating eye tissue within a capsular bag;
    a tubular curved section merged with the principal section for channeling the aspiration flow to the principal section;
    a tubular terminal section having an angled side face, substantially concentric about a longitudinal terminal axis and merged with the curved section for channeling the aspiration flow to the curved section, wherein the terminal axis is angled with respect to the principal axis;
    an aspiration bore at an extreme distal end of the terminal section for receiving the aspiration flow, the aspiration bore having a planar first end face and a planar second end face;
    an end fitting for coupling the needle to a conventional handpiece; and
    a transition section merged with the principal section for coupling the principal section to the end fitting and for channeling aspiration flow from the principal section to the end fitting.

7. The needle of claim 6:
    wherein the terminal axis forms an angle of approximately 5° to 35° with respect to the principal axis for accessing a larger area of the capsular bag when the surgical needle is rotated about the principal axis, for presenting the angled side face of the terminal section to eye tissue and increasing cavitational emulsification when the surgical needle is reciprocated along the principal axis, for maintaining visibility of the aspiration bore when viewed from above, and for maintaining a sufficient aspiration flow rate;
    wherein the planar second end face is tapered back at an angle of approximately 10°–45° with respect to a plane lying perpendicular to the terminal axis for opening up the aspiration bore to the direction of reciprocation, allowing the aspiration bore to be placed in close proximity with material to be emulsified, causing material to occlude and adhere to the aspiration bore, and helping the second end face to maintain contact with and mechanically emulsify the adhering material; and
    wherein the planar first end face is tapered back at an angle of approximately 0°–20° with respect to a plane lying perpendicular to the terminal axis for allowing the aspiration bore to be placed in close proximity with material to be emulsified, thereby increasing occlusion at the aspiration bore and increasing mechanical emulsification, and for presenting the first end face at a nearly parallel orientation to a capsular bag wall when the surgical needle is positioned close to the capsular bag wall to minimize the possibility of tearing the capsular bag wall.

8. The needle of claim 6, wherein the planar first end face is tapered back at an angle of approximately 0°–20° with respect to a plane lying perpendicular to the terminal axis for allowing the aspiration bore to be placed in close proximity with material to be emulsified, thereby increasing occlusion at the aspiration bore and increasing mechanical emulsification, and for presenting the first end face at a nearly parallel orientation to a capsular bag wall when the surgical needle is positioned close to the capsular bag wall to minimize the possibility of tearing the capsular bag wall.

9. The needle of claim 6, wherein the terminal section is approximately 5 mm long for accessing an adequate interior volume of the capsular bag when the needle is rotated about the principal axis, and wherein the needle further comprises a sleeve of flexible material encompassing a majority of the principal section for maintaining an irrigation flow about the needle in a direction countercurrent to the aspiration flow.

* * * * *